United States Patent [19]

Sutherland et al.

[11] Patent Number: 4,874,581

[45] Date of Patent: Oct. 17, 1989

[54] O₂/CO₂ CONTROL IN BLOOD OXYGENATORS

[75] Inventors: Karl M. Sutherland, Westminster; Matthew Jenusaitia, Irvine, both of Calif.

[73] Assignee: Baxter International Inc., Deerfield, Ill.

[21] Appl. No.: 216,070

[22] Filed: Jul. 7, 1988

Related U.S. Application Data

[63] Continuation of Ser. No. 874,288, Jun. 13, 1986, abandoned.

[51] Int. Cl.⁴ .............................................. A61M 1/32
[52] U.S. Cl. ....................................... 422/46; 422/47; 128/DIG. 3
[58] Field of Search ................................... 422/46–48; 261/DIG. 28; 128/DIG. 3

[56] References Cited

U.S. PATENT DOCUMENTS

| | | | |
|---|---|---|---|
| 4,254,081 | 3/1981 | Streczyn | 422/46 |
| 4,282,180 | 8/1981 | Raible | 422/47 |
| 4,440,722 | 4/1984 | Luppi | 422/47 |
| 4,612,170 | 9/1986 | Luther et al. | 422/46 |

FOREIGN PATENT DOCUMENTS

769786 5/1957 United Kingdom ................. 422/47

Primary Examiner—Michael S. Marcus
Attorney, Agent, or Firm—Michael C. Schiffer

[57] ABSTRACT

A blood oxygenator which independently controls the rate of oxygen and carbon dioxide exchange between an oxygen enriched gas and the blood. The oxygenator of the invention includes a gas inlet mechanism for diverting oxygen enriched gas between two different pathways. The first flow pathway feeds the oxygen bearing gas to a diffusion plate or sparger for the purpose of forming bubbles which diffuse into the blood to facilitate the exchange of oxygen and carbon dioxide between the gas and blood. The second flow pathway feeds oxygen down into the interior of the oxygenator as a substantially continuous stream which creates a substantially single gas bubble, or is simple a substantially continuous flow of gas with the oxygenator. This continuous flow of gas affects a gas exchange across the blood-gas interface, with carbon dioxide diffusing into the gas at substantially the same diffusion rate as occurs with the microbubbles diffusing into the blood, but with a lower diffusion rate for the oxygen.

8 Claims, 5 Drawing Sheets

$O_2/CO_2$ CONTROL IN BLOOD OXYGENATORS

This is a continuation of U.S. Pat. application Ser. No. 874,288, filed on June 13, 1986, now abandoned.

BACKGROUND OF THE INVENTION

This invention relates to a system for gas concentration control, and more particularly to an apparatus such as a blood oxygenator which allows for the independent control of oxygen ($O_2$) and carbon dioxide ($CO_2$) transfer with regard to the blood without increasing the amount of $O_2$ and $CO_2$ dissolved in the patients blood can be more precisely controlled.

In various types of surgical procedures it is often necessary to perform a treatment whereby the patients blood is subject to a bypass flow outside of the patients body, and an apparatus such as an oxygenator is employed. Such oxygenators are used in open-heart surgery and other operations and treatments of the body when it is necessary to establish an extracorporeal circulation system for temporarily assuming the functions of the heart and lungs of the patient. In such a system the oxygenator operates to perform the function usually performed by the lungs of the patient, i.e., the life-supporting transfer of oxygen into the blood and carbon dioxide out of the blood. The oxygenator is used in association with a pump which performs the function of the heart to cause circulation of the blood. Thus, early versions of the oxygenator were often referred to as "heart-lung" machines. The early heart-lung machines were typically rotating discs which passed through a pool of blood, but were only partially immersed therein such that the free surface of the disc exposed the blood to oxygen accomplished some gas transfer. After this, bag-type oxygenators were introduced which were superior to the disc oxygenators, but which left much to be desired.

At the present time two principle types of blood oxygenators are used which have proven efficient, provide minimal blood trauma, are convenient to set up and operate, are cost effective and have provided excellent clinical results, i.e. bubble oxygenators and membrane oxygenators.

In a membrane oxygenator, a thin, highly gas permeable membrane is placed between the gas and blood. Venous blood flows along one side of the membrane and gas is on the other side. A concentration gradient is established so that when the partial pressure for oxygen is higher in the ventilating gas than the partial pressure for oxygen in the venous blood, oxygen will diffuse across the membrane into the blood. Bubble oxygenators simply diffuse gas bubbles into venous blood. The oxygenated blood is typically defoamed before it is ready for delivery to the patient.

The typical bubble oxygenator is constructed of three chambers that are connected in series with each other, i.e. (1) a gas exchange or bubble chamber in which gas is dispersed as bubbles into the venous blood through small holes in a distributing manifold or sparger that is particularly used to create bubbles of the proper diameter and to disperse them effectively in the venous blood i.e., create foam and bubbles, and an effective mixture of gas and blood such that transfer o the oxygen into the blood takes place; (2) a defoaming or debubbling chamber wherein after gas transfer is completed, coalescence of the foam and the removal of the remaining bubbles is performed., and (3) a settling chamber in which the defoamed and oxygenated blood settles prior to being pumped back to the patient. Typically a heat exchange element is used in the bubble chamber for maintaining the blood temperature as for hypothermia.

Various prior art examples of blood oxygenators and gas-liquid type of transfer apparatus known in the art are described in U.S. Pat. Nos. 3,065,748 (illustrates two outlets 16 and 17), 3,256,883, 3,493,347 (two inlets 18 and 29), 4,073,622, 4,138,288, 4,182,739, 4,203,944, 4,203,945, 4,228,125, 4,231,988, 4,272,373 (separate inlets for gas and water), 4,336,224, 4,370,151, 4,374,088, 4,396,584, 4,407,777, 4.440,722, 4,493,692 (two separate sources for $O_2$ and $O_2/CO_2$) and 4,533,516.

In all bubble type blood oxygenators two types of gas transfer must take place. One is oxygen $O_2$) which is transferred into the blood and the other is carbon dioxide ($CO_2$) which is transferred out of the blood. Typically a bubble oxygenator provides a single gas inlet means for directing an oxygen bearing gas to a sparger which then disburses finely divided air bubbles into the blood. These bubble oxygenators also include an outlet means for carrying a gas bearing both oxygen and carbon dioxide out from the oxygenator.

In such presently available bubble oxygenators the one gas inlet only allows for the regulation of the gas flow to the sparger, and as a result for the control of the amount of the oxygen bearing gas microbubbles being delivered to the blood. This is generally performed by an adjustable gas valve positioned in the gas line. The amount of gas flowing to the blood directly affects the amount of oxygen delivery and carbon dioxide removal from the blood. In particular, microbubbles created by the sparger diffuse into the blood. The oxygen passes into the blood and the carbon dioxide passes into the bubbles through the bubble walls.

It is well recognized that the benefit of forming microbubbles from a given volume of gas is to maximize the total blood to gas interface area. That is, the rate of diffusion across the blood-gas interface, as defined by the bubble walls remains constant. By forming microbubbles the overall blood-gas interface area, as defined by the bubble walls is maximized for the given gas quantity.

The amount of oxygen delivered to the blood, as measured by the partial pressure of the oxygen ($PO_2$), as well as the amount of carbon dioxide being removed from the blood is increased by increasing the gas flow rate to the oxygenator. By decreasing the flow rate of the gas the amount of the oxygen delivery and carbon dioxide removal is reduced. However, during, for example, open heart surgery when the patient is being cooled or is cooled down, it does not take as much oxygen to oxygenate the blood of the patient. While under such conditions it is desirable to reduce the oxygen exchange rate, the rate of carbon dioxide removal from the blood remains the same or even increases during such operations. The disadvantage with presently available oxygenators is that such oxygenators do not possess the able to remove or blow off $CO_2$ without also having to increase the rate of oxygen exchange. That is, in order to blow off more $CO_2$, it is necessary to provide a higher gas flow rate which increases the amount of $O_2$ being delivered to the blood. Higher partial pressures of the $O_2$ are not wanted because of various undesirable side effects. It would therefore be desirable in a bubble oxygenator to be able to maintain the $CO_2$ removal from the blood while at the same time allowing for a lower $O_2$ transfer into the blood.

SUMMARY OF THE INVENTION

It is therefore an object of the present invention to provide a system for independently controlling the rate of oxygen and carbon dioxide exchange in an oxygenator.

Still another object of the present invention is to provide a procedure to independently control the rate of oxygen and carbon dioxide exchange in blood in a bubble oxygenator by providing for two flow pathways for the oxygen bearing gas being directed into the oxygenator, with the first flow pathway delivering the gas to the sparger, and the second flow pathway delivering a large volume of the gas to the interior region of the oxygenator.

The foregoing and other objects are accomplished in accordance with the features of the present invention by providing a blood oxygenator for mixing blood and an oxygen bearing gas to facilitate the absorption of the oxygen into the blood and absorption of the carbon dioxide from the blood into the gas.

The blood oxygenator of the invention includes a housing with at least a first blood inlet means and at least a first oxygen gas inlet means. Also provided is at least a first blood outlet means and at least a first gas outlet means to provide for the respective exodus for the now oxygenated blood and oxygen depleted gas. The oxygen gas inlet means further includes a variable gas flow means for diverting the gas flow between two different flow pathways.

The first flow pathway feeds the oxygen bearing gas to a diffusion plate or sparger which forms microbubbles. These bubbles diffuse into the blood thereby facilitating the diffusion of the oxygen into the blood and the carbon dioxide out of the blood. The second flow pathway feeds oxygen down into the interior of the housing. The gas forms a substantially single gas bubble, or is simply a substantially continuous flow of gas. The oxygenator is formed to ensure that the blood passing through the oxygenator comes into physical contact with this continuous flow of gas to affect a gas exchange across the blood-gas interface. The carbon dioxide diffuses across the blood-gas interface of the gas flow at substantially the same diffusion rate as would have occurred if a plurality of microbubbles were formed from the same volume of gas. However, the amount of oxygen diffusing across this interface is less than the amount which would have diffused across a plurality of microbubbles formed from the same volume of gas.

Thus the variable gas flow means provides an independent regulation of the amount of oxygen bearing gas flowing through each of the pathways, and thereby independently controls the diffusion rate of the oxygen and carbon dioxide across the gas bubble interface.

Examples of the bubble type blood oxygenator that can employ the features of the present invention are described in U.S. Pat. Nos. 3,468,631, 3,488,158 and 3,578,411, the last two of which describe devices which have come to be known as the Bentley Oxygenator, and U.S. Pat. Nos. 4,282,180 and 4,440,723, both assigned to Bentley Laboratories, Inc.

BRIEF DESCRIPTION OF THE DRAWINGS

For a better understanding of the invention as well as other objects and further features thereof, reference is made to the following detailed disclosure of this invention taken in conjunction with the accompanying drawings wherein.

DESCRIPTION OF THE PREFERRED EMBODIMENTS

Since the system described by the present invention has particular use in a bubble type blood oxygenator, the various features of the present invention including its use will be described within the environment of a bubble type blood oxygenator.

Figure 1:
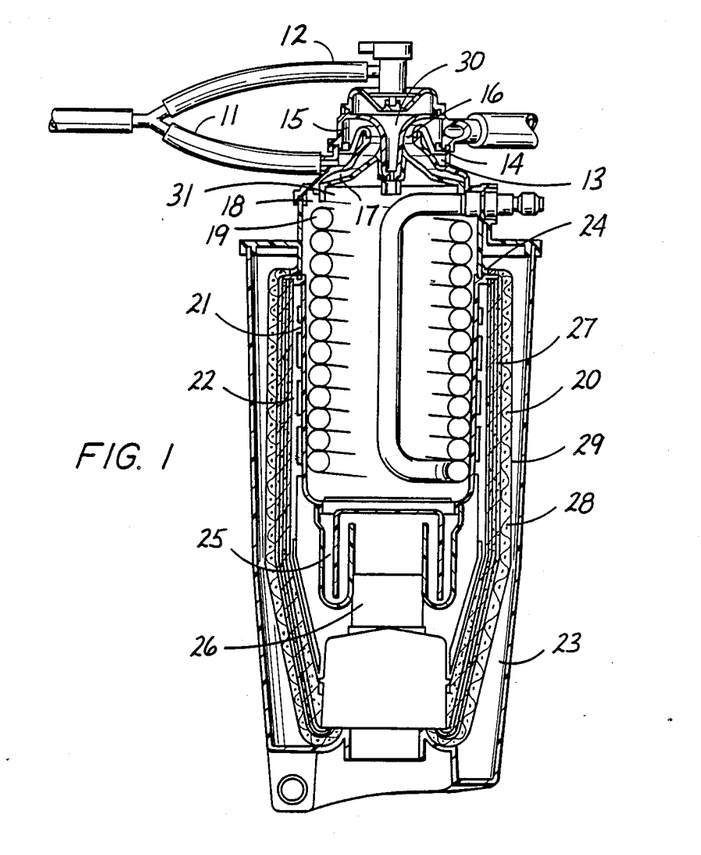
FIG. 1 is a plan sectional view of a bubble oxygenator taken along its axis which incorporates the features of the present invention and illustrates how the present invention is used with the oxygenator.

A bubble oxygenator is generally cylindrical in configuration and comprises an outer shell which is provided with a gas inlet and a blood inlet. Other inlets and outlets are generally provided such as an inlet for priming as well as for optimal medication administration and, if needed, a return inlet from a cardiotomy reservoir. Blood outlets and a gas vent are also provided. There is also an inlet for heat exchanger fluid and an outlet for such fluid.

referring now to FIG. 1, the internal construction of a bubble oxygenator 10 is shown in more detail. As illustrated, gas (oxygen) flows into the oxygenator through a gas inlet mechanism which in accordance with the features of the present invention consists of two gas inlets 11 and 12, inlets 11 and 12 define the two separate pathways the specific features and operation of which will be explained in detail hereinbelow. The gas inlet 11 typically connects with annular chamber 13 which is bounded on its upper end by a sparger or diffusion means 14. This diffusion means 14 may be constructed of a plate of suitable porous material or a perforated apertured member, but preferabley is a plate with three circular patterns containing 66 perforations which are 0.010 inches in diameter and 6 perforations which are 0.025 inches in diameter, the larger perforations being more or less uniformly distributed among the smaller perforations.

Blood inlet means (generally two inlet orifices connected to the very top portion of the oxygenator, which are not specifically shown in FIG. 1) contact with the interior of annular chamber 15 in a generally tangential manner. Thus, when chamber 15 is filled with blood, flowing in a spiral manner, and gas is admitted to the device 10 through inlet 11, the gas, such as oxygen or an oxygen rich mixture, passes through inlet 11, into chamber 13 and through diffusion means 14 into the body of blood in chamber 15. Bubbles are formed in chamber 15 when the ga enters the blood.

Chamber 15 connects with annular channel 16 and undulating distribution channel 17, the latter generally being conical in shape. Channel 17 connects with annular mixing chamber IB which is provided with heat exchange tubing 19. Heat exchange tubing 19 is preferably a smooth and coiled helically wrapped tubing which provides for a helically descending flow path of the blood through the bubble column.

At the lower end of chamber 18, the outer wall of this chamber terminates approximately two-thirds of the distance from the top to the bottom of the oxygenator to permit the bubbles of blood to come into contact with defoaming means 20. While several defoaming means may be used, e.g., that disclosed in U.S. Pat. No. 3,468,631, it is preferred in one embodiment of the present invention to form the defoaming material from a polyurethane foam having about ten to thirty pores per inch. The polyurethane foam and the other defoamer parts are coated with a silicone defoaming agent. Optionally, a spacer may be provided between defoaming material 20 and wall 21. The spacer may comprise a ribbed structure which provides open space therebetween.

Open spaces are provided in space 22 which permit blood to come into contact with defoaming material 20. The lower end of the oxygenator 10 is provided with reservoir 23 where oxygenated liquid blood is collected for subsequent return to the patient.

An annular passage (not shown) so that vent gases (e.g. oxygen or carbon dioxide) may be exhausted from the oxygenator. A mesh sleeve which may be of a polyester, polypropylene, polyethylene, nylon or other suitable fabric is positioned around defoaming material 20 and is provided with nylon bands 24 to hold it in place.

In order to obtain the desired gas transfer and be able to separately control oxygen transfer to the blood and carbon dioxide transfer out of the blood independently of one another in accordance with the features of the present invention, the two separate gas inlets 11 and 12 are connected to oxygenator 10 for the purpose of supplying oxygen or an oxygen-rich gas to the oxygenator through two separate pathways. The first oxygen inlet 11 preferably directs the oxygen enriched gas through the so-called normal location for feeding the oxygen enriched gas to the oxygenator sparger or diffusion means 14. The second oxygen inlet 12 includes a valve which can be operated to vary the amount of gas that flows through this second inlet 12 from about 0 (in which case all the oxygen gas will flow through the first oxygen inlet 11) to about 90 percent of the total gas flow to the oxygenator.

During normal operation of oxygenator 10 all of the oxygen fed to the oxygenator is fed through the first oxygen inlet 11. When the demand for oxygen transfer to the blood is lowered, and the need for carbon dioxide transfer out of the blood is constant or increases (e.g. when the patient during surgery is on a bypass apparatus and his blood and body temperature is cooled), the oxygen enriched gas is redirected to flow into both the first and second oxygen inlets 11 and 12 at the appropriate proportions by adjusting the valve.

This causes the oxygen enriched gas to flow through both of the pathways, with the percentage of flow rate through each pathway being dependent upon the degree at which the valve is open. That is, when the valve is fully open more of the gas will flow through the second pathway in comparison to when the valve is only slightly open. This allows the user to adjust the flow rate depending upon whether the need exists to deliver additional oxygen to the patient.

When the gas is directed to flow through the second pathway the gas is delivered directly into the oxygenator. That is, the gas is not sparged to create numerous microbubbles, but for a substantially continuous stream or mass flowing through the oxygenator.

In the illustrated embodiment the gas is delivered into that region of the oxygenator defined by the inner surfaces of the heat exchange coil 19. As the gas enters the oxygenator it at least partially fills this region. The blood which is passing over the exterior surface of the coil 19 comes into contact with the gas between the various turnings of the coil 19. It is at these various locations that the exchange of the carbon dioxide and oxygen can occur. The carbon dioxide will easily pass across the blood-gas interface because of the generally low concentration of carbon dioxide carried by the gas. The oxygen will also pass easily across this interface because of the generally low concentration of oxygen in the blood. However, the rate of exchange of the oxygen will not be as great in comparison to the exchange rate with microbubbles because of the lower surface area as defined by the blood-gas interface. Nevertheless, it has been found that the exchange rate for the carbon dioxide remains substantially the same despite this lower surface area.

It should be noted that in accordance with the present invention, the proportion or split of percentage of gas flowing into each inlet, as thus through each pathway, will vary depending on the particular requirements for gas exchange. For example, this proportion can vary from about 100 percent gas through inlet 11 and 0 percent gas through inlet 12, to about 10 percent or less gas through inlet 11 to about 90 percent or more gas through inlet 12. The precise amount of gas flowing through each inlet and thus each pathway is dependent not only upon the proportion of the split between each inlet but also upon the overall gas flow rate being delivered to the oxygenator. The effect of this ratio becomes even greater if the amount of gas flow must be increased to obtain the desired carbon dioxide levels in the blood.

The operation of oxygenator 10 when employing the features of the present invention is as follows: The first oxygen inlet 11 directs the oxygen which is fed through it into the oxygenator and through the apertures in diffusion means 14. The diffusion means then creates very small bubbles to mix with the incoming blood in chamber 15 and to allow for the diffusion of oxygen into the blood and for the removal of carbon dioxide from the blood. The oxygen enriched blood then flows through a torturous path which directs it down onto the heat exchanger tubing or coil 19.

At this time the blood may be heated or cooled as desired. The blood continues to flow downward and through a gas expander chamber 25 and through a micro emboli inhibitor plug 26. Thereafter the blood travels preferably through a three stage defoamer 20 constructed of, for example, a polyester mesh 27, polyester foam 28 and a polyester tricot sock 29. The defoamer 20 separates the blood and gas allowing the gas to be vented off and the blood to enter reservoir 23 there it is then pumped back to the patient.

When the second oxygen inlet 12 to oxygenator 10 is opened via the valve connected thereto a portion of the oxygen enriched gas flows into the valve and into the top portion of the oxygenator. This gas then flows into chamber 30 and then into chamber 31. What this causes is a reduced amount of oxygen enriched gas being forwarded through the first oxygen inlet 11 which passes through the sparger 14 forming microbubbles. With the reduction in the concentration of microbubbles in the blood the rate of oxygen transfer as measured by the partial pressure of oxygen in the blood is reduced. However, it has been found that despite this reduction in oxygen transfer the rate of carbon dioxide transfer stays relatively unchanged since it appears not as strongly associated with the blood-gas interface.

Thus an oxygenator incorporating the gas regulating mechanism and the two separate pathways in accordance with the invention allows for the separate and independent control of oxygen and carbon dioxide transfer.

Figure 2:
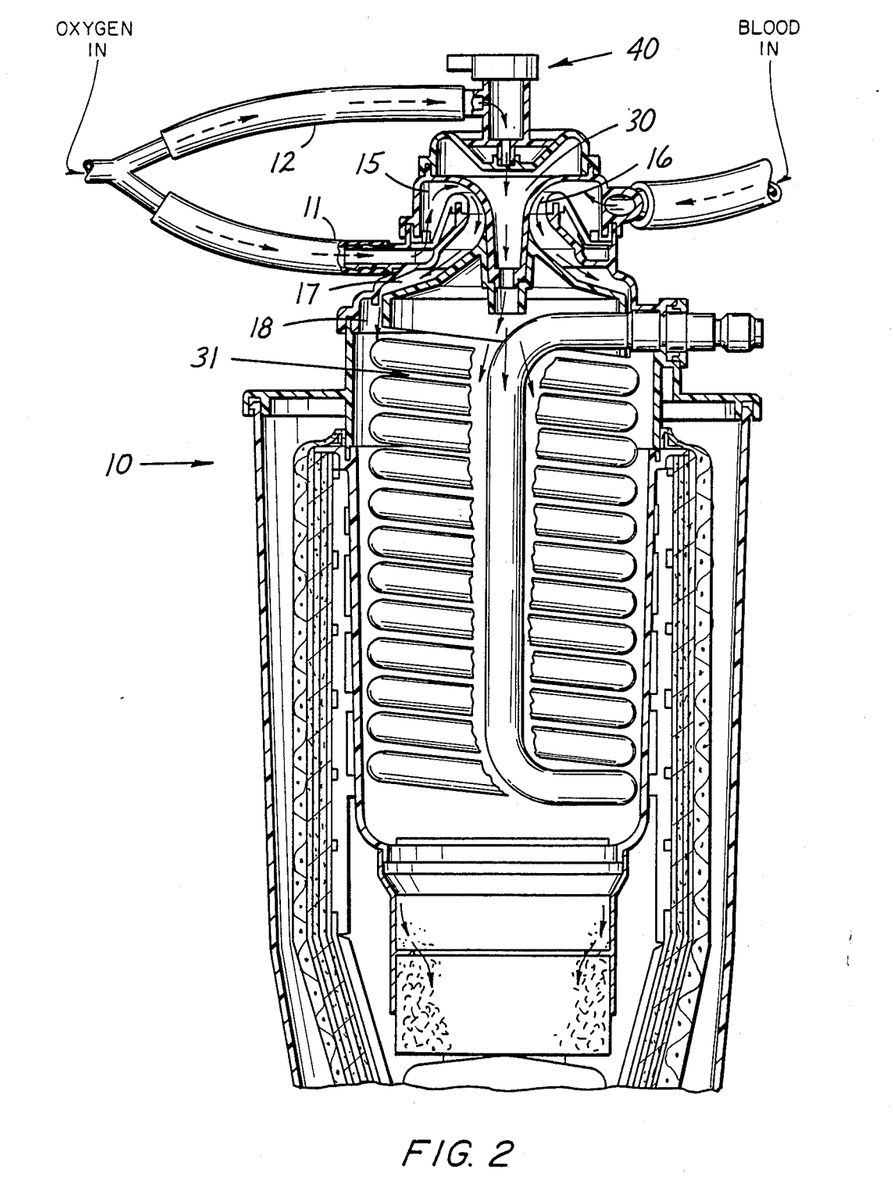
FIG. 2 is an enlarged plan sectional view of a bubble oxygenator as shown in FIG. 1 illustrating the flow of oxygen through the device., FIG. 3. is a plan sectional view of the type of gas splitter valve that is used with the bubble oxygenator shown in FIG. 1 to divert oxygen gas flow to the center of the oxygenator shown in FIG. 1.

Specific details clearly illustrating the oxygen flow into and through the oxygenator 10 when oxygen is fed through a first oxygen inlet 11 and a second oxygen inlet 12 is clearly shown by the arrows in FIG. 2 which represent oxygen flow.

Figure 3:
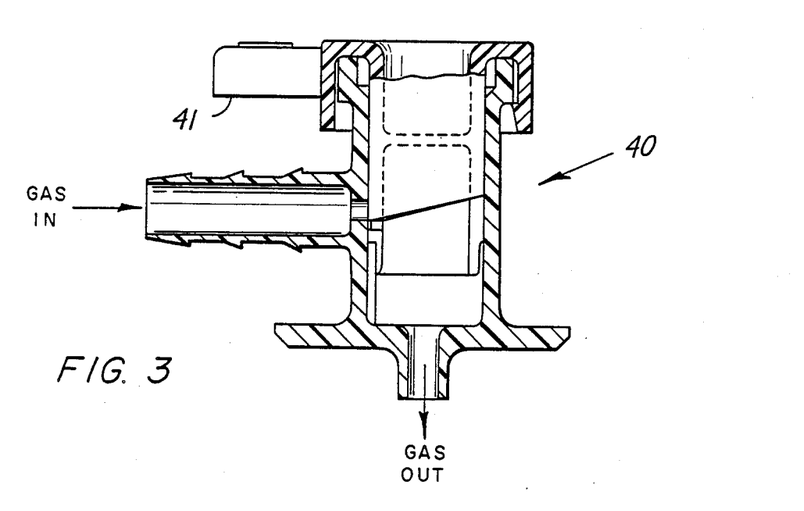

The type of splitter mechanism which can be used with the features of the present invention to control the oxygen flow to inlets 11 and 12 divert oxygen gas flow to the center of the oxygenator 10 is shown as splitter 40 in FIG. 3. This function is achieved by using a small orifice that gradually opens as the handle 41 on top is turned. The amount of oxygen that can enter the oxygenator 10 is a function of the oxygen pressure, orifice size and back pressure in the unit.

Referring now to FIGS. 4-9 another embodiment of the invention will be described, as well as a discussion concerning experimental data illustrating the rates for oxygen and carbon dioxide exchange between a prior art oxygenator and an oxygenator constructed in accordance with the instant invention.

Figure 4:
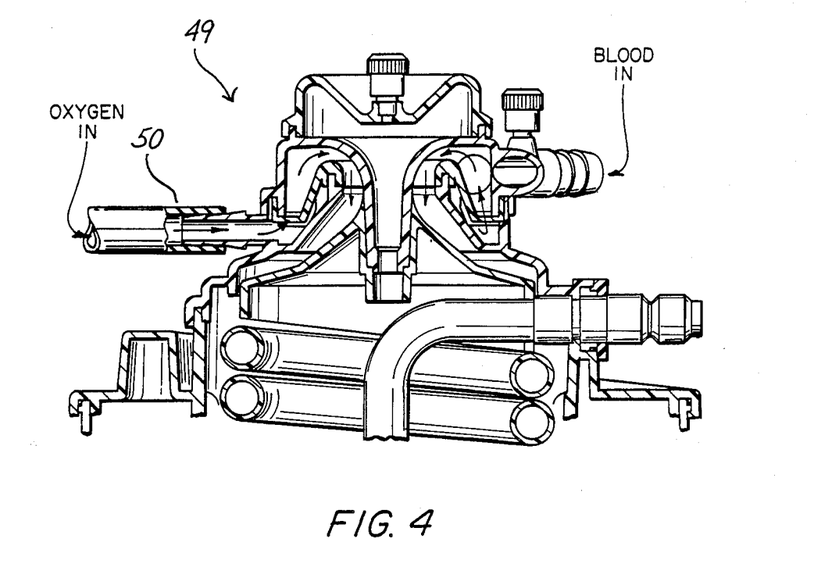
FIG. 4 is a plan sectional view of the gas and blood inlet ports of an oxygenator in accordance with presently available technology.
Figure 5:
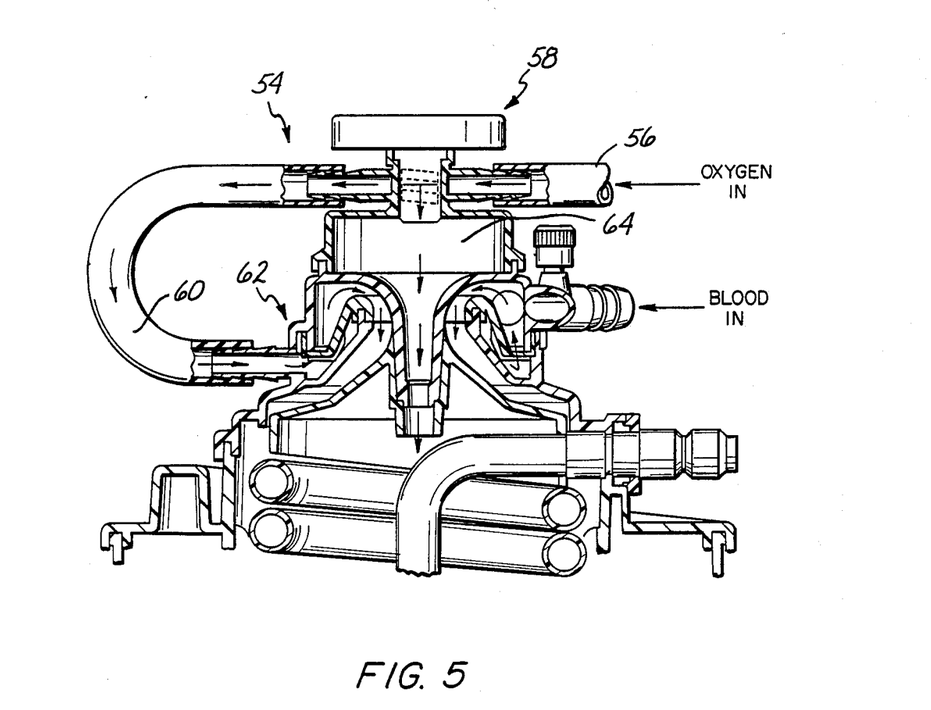
FIG. 5 is a plan sectional view of gas and blood inlet ports of an oxygenator in accordance with another embodiment of the invention.

FIGS. 4 and 5 illustrate the prior art and present oxygenators, as seen at 49 and 54 respectively. Both of these oxygenators have components which are similar to the oxygenator described above and illustrated in FIG. 1, except for the oxygen enriched gas inlet means. In particular the oxygenators have a housing, heat exchange coil, blood inlet means, sparger and gas and blood outlet means which are similar to the same components of the oxygenator of FIG. 1, and as such will not be described any further. Furthermore, both of these oxygenators are manufactured and sold by Baxter Healthcare Corporation of Deerfeild, Ill., with oxygenator 49 being sold under the designation Bentley-10B ™, and the oxygenator 54 being sold under the designation Bentley-10 Plus ™.

The oxygenator illustrated in FIG. 4 is constructed with a typical gas inlet port and conduct which directs the gas to the sparger, while the oxygenator illustrated in FIG. 5 includes a gas inlet means which has a valve for directing the gas between two or more pathways, one of which leads to a standard sparger.

The gas inlet means, seen generally at 50, of the oxygenator 49 (as seen in FIG. 4) is basically a single port which directs the gas to the sparger, seen generally at 52. Thus the oxygenator 49 can only regulate the rate of oxygen and carbon dioxide exchange by regulating the flow rate of the oxygen enriched gas to the oxygenator 49 by increasing or decreasing the flow rate through the inlet means or port 50. As stated above this type of arrangement does not allow for the independent regulation of the oxygen and carbon dioxide exchange rate. Thus, when the gas flow rate is reduced both the oxygen and carbon dioxide exchange rates drop, while the opposite occurs by increasing the gas flow rate.

The oxygenator 54, as seen in FIG. 5 is the preferred embodiment of the present invention. Unlike the embodiment illustrated in FIG. 1, oxygenator 54 includes a single gas line 56 which is connected to a two-way valve 58. This preferred embodiment allows for a more efficient control of the flow rate between the two pathways 60 and 64. The two-way valve 58 can be operated to direct all or a portion of the oxygen enriched gas either to the fluid pathway 60 which leads to the sparger 62, or to the fluid pathway 64 which directs the gas to the interior of the oxygenator 54.

The oxygen enriched gas can be directed to the sparger 62 which forms the microbubbles, which as stated allows for a sufficient exchange of both the oxygen and carbon dioxide. This aspect of the invention is the same as with presently available oxygenators, for the example the oxygenator 49 illustrated in FIG. 4. On the other hand a portion of the gas can be directed to pass through the second pathway 64. The gas enters the oxygenator through this pathway in a substantially continuous stream, to form in essence a substantially single bubble. This provides for essentially the same carbon dioxide exchange, but results in a diminished exchange rate for the oxygen.

Referring now to FIGS. 6-9 data demonstrating the independent control of the oxygen and carbon dioxide exchange rates will be discussed. These figures illustrate individual graphs showing the oxygen and carbon dioxide exchange rates for the oxygenator 49 illustrated in FIGS. 8 and 9, and for the oxygenator 54 illustrated in FIGS. 6 and 7.

Figure 6:
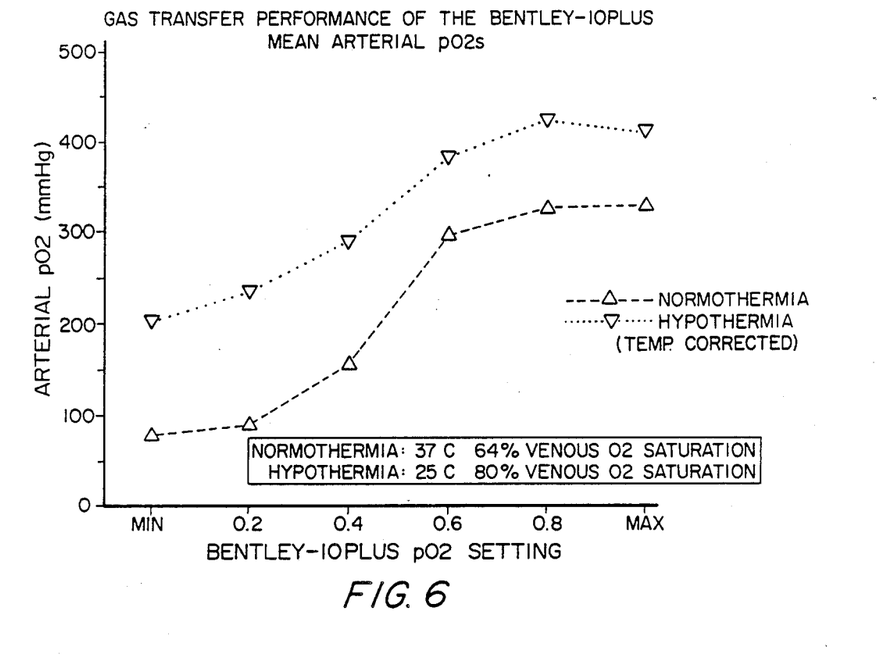
FIGS. 6 and 7 are graphs illustrating the partial pressure of oxygen and the carbon dioxide gas transfer rate for blood oxygenated using the oxygenator having the gas regulating valve means in accordance with the invention illustrated in FIG. 5.
Figure 7:
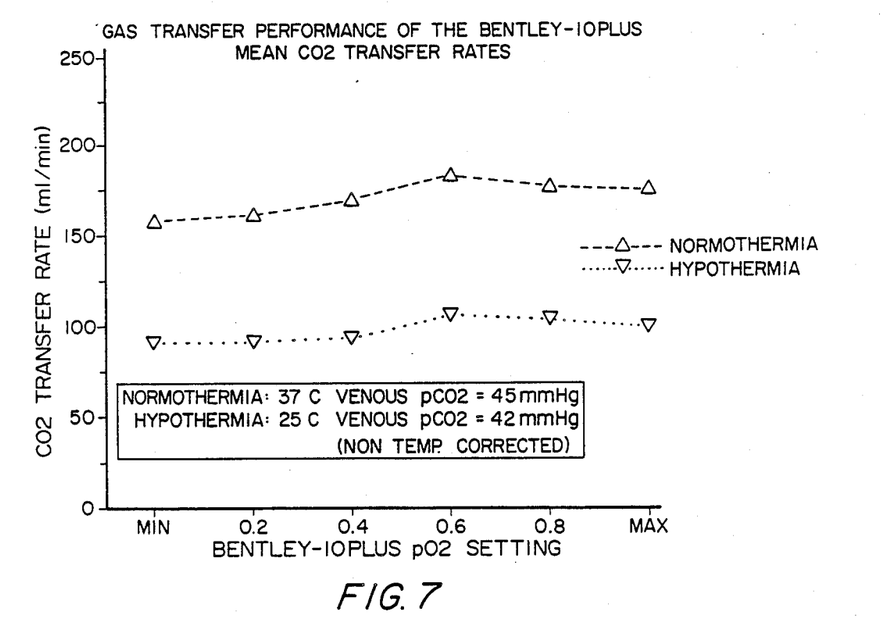

The graphs in FIGS. 6 and 7 illustrate the oxygen and carbon dioxide exchange rates at two different blood temperatures, that being normothermia (37° C.) and hypothermia (25° C.), and for different flow rates between the two different pathways of the oxygen enriched gas. The different blood temperature levels are specified by the two different lines. The X coordinate for both graphs (FIGS. 6 and 7) pertains to a variance in the flow rate between the two pathways, with the indicated intervals corresponding to a variance of about 15% in the flow from one pathway to the other. Specifically, the flow rate deviates between the maximum (max.) setting of 100% through the first pathway to the sparger to the minimum (min.) setting of only 20% through the first pathway to the sparger and 80% to the second pathway. The graph starts at the minimum setting, that is the level at which the gas flows primarily through the second pathway, and gradually goes up at the selected intervals to the maximum setting, that is the level at which the gas flows primarily through the first pathway to the sparger.

As seen in FIG. 6 the oxygen exchange, which is measured by standard procedures for determining the partial pressure of oxygen in the blood, gradually increases and then levels off as the oxygen enriched gas flow is directed in increasingly 20% increments from the second pathway to the first pathway, and thus to the sparger. FIG. 7 shows that the carbon dioxide ($CO_2$) exchange for the same flow rate changes remains substantially constant despite the proportional flow rate change from the second pathway to the first pathway.

Figure 8:
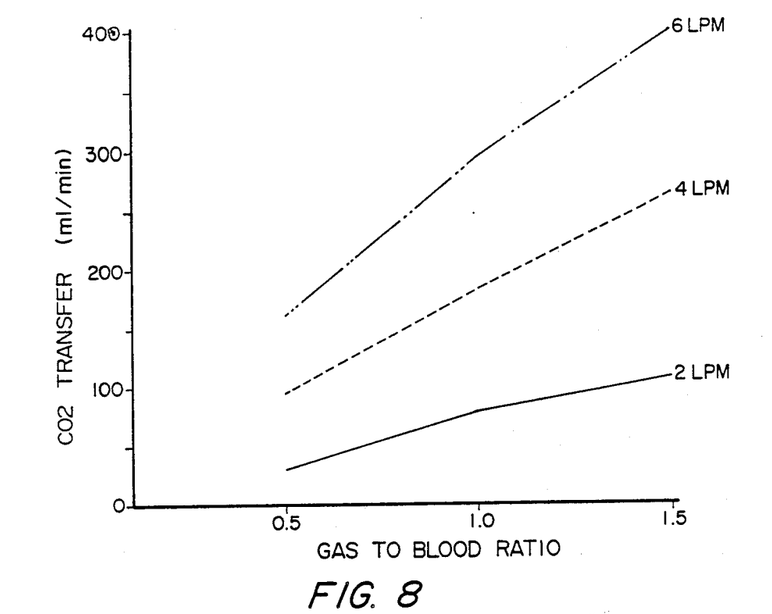
FIGS. 8 and 9 are graphs illustrating the partial pressure of oxygen and the carbon dioxide gas transfer rate for blood oxygenated using the oxygenator illustrated in FIG. 4.
Figure 9:
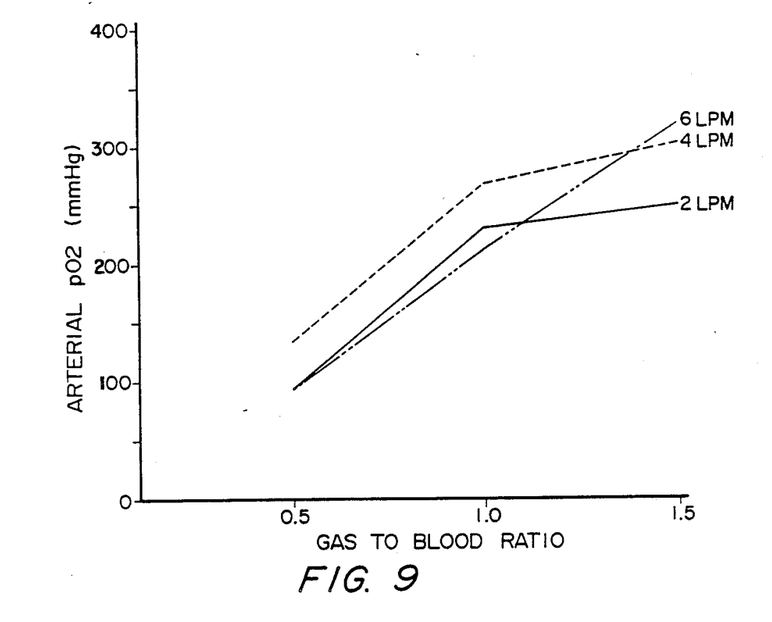

However, this is dissimilar to what occurs with presently available oxygenators, for example oxygenator 49. The results of varying the oxygen enriched gas flow rate to the oxygenator, in order to control the oxygen and carbon dioxide exchange rates is seen in the graphs of FIGS. 8 and 9.

In these graphs the X-coordinate indicates the overall flow rate of the oxygen enriched gas to the oxygenator 49, with all of the gas being delivered to the sparger. The flow rate indicated along the X-coordinate is the actual amount of gas being delivered for the volume of blood in the oxygenator. The graphs also indicate the exact flow rate which is specified in litres per minute (LPM) at each graph line. The results indicated in these graphs are for normothermia (37° C.). As seen from these Figures the rate of oxygen absorption, as measure by the partial pressure of oxygen in the blood, as well as the carbon dioxide exchange rate both gradually increase as the gas volume or flow rate increases.

These graphs thus demonstrate that an oxygenator including the dual fluid flow pathways in accordance with the instant invention provide the desired independent control of the oxygen and carbon dioxide absorption or exchange rate. It should be noted that the instant invention can also provide for the lowering of the carbon dioxide exchange rate by merely decreasing the overall flow rate of the oxygen enriched gas to the oxygenator, as is typically performed with presently available oxygenators.

While the preferred embodiments have been described, various modifications and substitutions may be made thereto without departing from the scope of the invention. Accordingly, it is to be understood that the invention has been described by way of illustration and not limitation.

What is claimed is:

1. A blood oxygenator comprising:
   a housing which defines a blood receiving compartment, said housing having blood inlet and outlet ports which communicate with said blood receiving compartment through which blood enters and exits said compartment, said housing further having a plurality of gas inlet ports which communicate with said blood receiving compartment through which an oxygen enriched gas enters said compartment;
   means which selectively communicates with said gas ports for defining at least two gas flow pathways through said compartment;
   a difuser means associated with a first of said pathways which is operable for fractioning said gas into a plurality of microbubbles which are dispersed in any of said blood in said compartment;
   a gas feed means associated with a second of said gas pathways which is operable for dispersing a substantially continuous, unsparged defined volume of gas in any of said blood in said compartment separate from said microbubbles dispersed in said body by said fractioning means;
   wherein said housing compartment includes first a second portions for receiving said blood from said blood inlet ports, said first portion being positioned to receive said plurality of microbubbles from said diffuser means, and said second portion being positioned to receive said substantially continuous, unsparged flow of gas from said gas feed means, said first and second portions being in at least partial fluid communication; and
   means associated with both of said gas flow pathways which is operable for controlling the flow of gas between said pathways.

2. The oxygenator of claim 1 further including a means positioned in said housing compartment which is positioned to engage said blood entering said housing compartment for regulating the temperature of said blood.

3. The oxygenator of claim 2 wherein said temperature regulating means defines said second portion of said compartment, with said second portion fluidially communicating with said first portion in a manner such that said blood passing through said first portion flows across said regulating means to facilitate said temperature regulation and passes partially into said second portion.

4. The oxygenator of claim 3 wherein said temperature regulating means defines a cavity as said second portion within said compartment into which gas flows from said second gas flow pathway, said cavity being defined by said regulating means to provide locations which are at least partially in fluid contact with said blood flowing across said regulating means surface.

5. The oxygenator of claim 4 wherein said second portion is formed to minimize mixing of said gas and said blood.

6. A blood oxygenator comprising:
   a housing which defines at least a first compartment for received blood from a patient having one or more blood ports through which blood enters and exits said compartment, said housing further including one or more ports for directing an oxygen enriched gas into said housing for gas exchange contact with said blood;
   a heat exchange means positioned in said housing first compartment which is positioned to engage said blood entering said compartment, said heat exchange means being operable for heating or cooling said blood, said heat exchange means being formed to define a subcompartment of said housing first compartment, which subcompartment is in fluid communication with said housing first compartment to receive a portion of said blood from said housing first compartment;
   means communicating with said gas inlet ports for defining at least two gas flow pathways in said housing through which said oxygen enriched gas may be selectively directed, a first layer of said pathways including a means disposed in said first housing compartment which is operable for fractioning said gas into a plurality of microbubbles into said blood, a second of said pathways including a means which is operable for directing a substantially continuous, unsparged flow of said gas into said sub-compartment for contact with said blood.

7. The oxygenator of claim 6 wherein said regulating means is defined as a body about which said blood in said first portion flows, which body defines said second portion and provides fluid contact between said blood and said gas flowing into said second portion from said second gas flow pathway.

8. The oxygenator of claim 7 wherein said regulating means is a heat exchange coil.

* * * * *